United States Patent [19]
Bielefeldt et al.

[11] Patent Number: 4,970,337
[45] Date of Patent: Nov. 13, 1990

[54] PROCESS FOR THE PREPARATION OF TRIFLUOROMETHANESULPHONYL CHLORIDE

[75] Inventors: Dietmar Bielefeldt, Ratingen; Albrecht Marhold, Leverkusen, both of Fed. Rep. of Germany

[73] Assignee: Bayer Aktiengesellschaft, Leverkusen, Fed. Rep. of Germany

[21] Appl. No.: 271,976

[22] Filed: Nov. 16, 1988

[30] Foreign Application Priority Data

Dec. 5, 1987 [DE] Fed. Rep. of Germany ....... 3741309

[51] Int. Cl.$^5$ ............................................ C07C 143/70
[52] U.S. Cl. ................................................... 562/829
[58] Field of Search ..................... 260/543 R; 582/829

[56] References Cited

U.S. PATENT DOCUMENTS 2,277,325  3/1942  Hueter et al. ...................... 260/543
3,130,221  4/1964  Oesterling ...................... 260/543 R
4,699,736 10/1987  Gongora et al. .................... 562/829

FOREIGN PATENT DOCUMENTS 0040560 11/1981 European Pat. Off. .

OTHER PUBLICATIONS

Journal of the Chemical Society, Chairman: C. K. Ingold, D. Sc., F.R.I.C., F.R.S. 1955, Part III, pp. 2085-3312.

Primary Examiner—Paul J. Killos
Attorney, Agent, or Firm—Sprung Horn Kramer & Woods

[57] ABSTRACT

Trifluoromethanesulphonyl chloride is prepared by reacting bis-(trifluoromethyl)-disulphane with chlorine and water in the liquid phase.

15 Claims, No Drawings

PROCESS FOR THE PREPARATION OF TRIFLUOROMETHANESULPHONYL CHLORIDE

The present invention relates to a process for the preparation of trifluoromethanesulphonyl chloride from bis-(trifluoromethyl)-disulphane.

Trifluoromethanesulphonyl chloride is a universally utilizable chemical which is employed, for example, for the preparation of organic intermediates (see Gmelin, Handbuch der anorganischen Chemie (Handbook of Inorganic Chemistry), volume Fluorine B12, 144 (1973)).

Processes for the preparation of trifluoromethanesulphonyl chloride have already been disclosed. Thus $CF_3SCl$ can be reacted with an excess of chlorine and water in the course of 7 days and trifluoromethanesulphonyl chloride can be obtained (see US-PS 2,732,398). Trifluoromethanesulphonic acid or its salts can also be chlorinated with phosphorous pentachloride (see R.N. Haszeldine et al., J. Chem. Soc. 1955, 2901 to 2910 and G.v. Dyke Tiers, J. Org. Chem. 28, 1244 to 1246 (1963)). Furthermore, trifluoromethanesulphonyl fluoride can be reduced using hydrazine and the resulting intermediate can be cleaved using chlorine (see US-PS 2,950,317) or trifluoromethanesulphonic anhydride can be reacted with sodium chloride in tetramethylene sulphone.

The disadvantage of these processes is that they can only be carried out with poor space-time yields, require starting products or re-agents which are not easily accessible and/or yield salt-like by-products which have to be disposed of in a complicated manner.

A process for the preparation of trifluoromethanesulphonyl chloride has now been found which is characterized in that bis-(trifluoromethyl)-disulphane is reacted with chlorine and water in the liquid phase.

The starting product bis-(trifluoromethyl)-disulphane required for the process according to the invention is known and accessible in a simple manner. It is obtained, for example, as a previously undesired by-product in the preparation of $CF_3SCl$ (see W. Tullock and D.D. Coffmann, J. Org. Chem., 25, 2016 (1960)) by fluorination of trichloromethylsulphenyl chloride with sodium fluoride (see US-PS 2,884,453) or by fluorination of bis-(trichloromethyl)-disulphane with hydrogen fluoride (see DE-OS (German Published Specification) 1,232,954 and Synthesis 6, 310 (1972).

The liquid phase necessary according to the invention can be verified, for example, by working in the presence of a solvent which is able to dissolve chlorine and water in sufficient quantities and is inert towards chlorination. 1,2-dichloroethane, for example, is suitable for this.

Preferably, the process according to the invention is carried out in an acidic medium, for example in the presence of strong acids. If these acids are employed as aqueous acids in an appropriate concentration and amount, then the water required can also be introduced into the reaction by means thereof. Suitable acids are, for example, sulphuric acid, nitric acid, hydrochloric acid, phosphoric acid, methanesulphonic acid, acetic acid and organic and inorganic acids containing fluorine and/or chlorine such as fluoroacetic acids, chloroacetic acids, perfluoroalkanesulphonic acids, fluorosulphonic acids and chlorosulphonic acids. Mixtures of two or more acids can also be employed.

Aqueous sulphuric acid in concentrations of 5 to 70% by weight, aqueous nitric acid in concentrations of 5 to 90% by weight, aqueous hydrochloric acid in concentrations of 5 to 39% by weight, aqueous phosphoric acid in concentrations of 30 to 85% by weight, aqueous acetic acid in concentrations of 30 to 95% by weight, aqueous di- and/or trifluoroacetic acid in concentrations of 5 to 100% by weight and/or aqueous mono-, di- and/or trichloroacetic acid in concentrations of 5 to 95% by weight are preferred.

The chlorine can be added to the process according to the invention in liquid or gaseous form, if desired also in the form of compounds or mixtures which yield chlorine in situ under the reaction conditions of the process according to the invention. Examples hereof are sodium hypochlorite or chlorinated lime, in each case combined with hydrochloric acid.

Stoichiometrically, 4 moles of water are required in the process according to the invention for the reaction of one mole of the disulphane. For example, at least 3.5 moles, preferably at least 4 moles, of water are employed per mole of disulphane. Above this, the amount of water is not critical. For example, up to 100 moles and more of water can be employed per mole of the disulphane. The water can be added to the reaction mixture as such, but can also be used, for example, mixed with a solvent, for example 1,2-dichloroethane and/or in the form of an aqueous solution.

Stoichiometrically, 5 moles of chlorine are required in the process according to the invention for the reaction of 1 mole of disulphane. For example, at least 4 moles, preferably at least 5 moles, of chlorine are employed per mole of disulphane. Above this, the amount of chlorine is not critical. For example, up to 30 moles and more of chlorine can be employed per mole of disulphane.

If it is intended to work in the presence of acids, then, for example, 0.1 to 20 parts by weight of acid (calculated as 100% strength acid) can be employed per part by weight of the disulphane.

The process according to the invention can be carried out, for example, at temperatures in the range from $-18°$ to $+120°$ C. Temperatures in the range from $0°$ to $80°$ C. are preferred. At temperatures above $40°$ C. it is advantageous to work in closed vessels or under pressure (for example at up to 100 bar) in order to suppress escape of volatile components.

The process according to the invention can be carried out both continuously and batchwise. The reaction time can be, for example, between 2 and 72 hours.

In a particular embodiment of the process according to the invention, the reaction is carried out in the presence of a catalyst. Fluorinated sulphonamides are preferably used as catalysts. Catalysts of this type can be employed, for example, in amounts from 0.1 to 20 parts by weight per part by weight of the sulphane.

Working up can be carried out, for example, by initially, if necessary, separating off any chlorine which is still present, for example by distillation or blowing out with nitrogen, and then separating the two phases present, for example by phase separation and/or distillation. The organic phase which is separated off in general consists of trifluoromethanesulphonyl chloride which is so pure that it can be used directly for further reactions.

Suitable vessel materials for carrying out the process according to the invention are, for example, steel, Hasteloy ®, glass, Teflon ® and vessels lined with lead or enamel. Glass, Teflon ® or vessels lined with lead or enamel are preferably used.

The process according to the invention is distinguished in that it starts out from easily accessible starting materials and permits the preparation of trifluoromethanesulphonyl chloride in good yields and without the formation of salt-like by-products.

The process according to the invention permits the preparation of trifluoromethanesulphonyl chloride in a simple manner, in good to very good purities and in advantageous yields. The process according to the invention is furthermore distinguished in that it can be carried out at relatively low temperatures and in that it is advantageous with respect to corrosion problems and energy costs. Moreover, it permits the preparation of trifluoromethanesulphonyl chloride on an industrial scale from a starting product for which no industrial use was previously known.

It is very surprising that the advantages demonstrated can be realized by the process according to the invention, since in J. Chem. Soc. 4230 (1954) it is stated that no reaction occurred in the experiment on the oxidation of bis-(trifluoromethyl)-disulphane using concentrated nitric acid and only unidentified decomposition products are found at high temperatures.

The following examples illustrate the process according to the invention without limiting it thereto.

EXAMPLES

Example 1

430 g of gaseous chlorine were passed into a mixture of 500 ml of concentrated aqueous hydrochloric acid, 410 g of bis-(trifluoromethyl-)disulphane and 5 g of nonafluorobutanesulphonamide at 20° C., with continuous stirring. After completion of the addition of chlorine, the organic phase was separated from the aqueous phase and washed with ice water. 317 g of trifluoromethanesulphonyl chloride (86.4% pure) having a boiling point of 31° to 33° C. at 1013 bar were obtained.

Example 2

205 g of gaseous chlorine were passed into a mixture of 200 ml of aqueous concentrated hydrochloric acid and 100 g of bis-(trifluoromethyl-)disulphane, with continuous stirring, at 40° C., in the course of 21 hours. After the end of the addition, the organic phase was separated off and washed with ice water. 123.5 g of trifluoromethanesulphonyl chloride having a purity of 99% were obtained. The product can be employed for virtually all applications without further purification.

Example 3

195 g of gaseous chlorine were metered into a mixture of 200 ml of concentrated hydrochloric acid, 100 g of bis-(trifluoromethyl-)disulphane and 5 g of allylheptadecafluorooctanesulphonamide, with continuous stirring, at 20° C., in the course of 24 hours. After completion of the metering in, the organic phase was separated off. 108 g of trifluoromethanesulphonyl chloride having a purity of 99.3% were obtained. This product can be used for virtually all applications without further purification.

Example 4

50.5 g of bis-(trifluoromethyl-)disulphane, 57 ml of liquid chlorine and 5 g of nonafluorobutanesulphonamide were dissolved in 250 ml of concentrated aqueous hydrochloric acid in an autoclave made of Teflon ®. The mixture was heated to 120° C. and kept at this temperature for 8 hours. After phase separation, 57 g of trifluoromethanesulphonyl chloride having a purity of 99% were obtained as the organic phase.

What is claimed is:

1. A process for the preparation of trifluoromethanesulphonyl chloride, consisting essentially of reacting (trifluoromethyl-) disulphane with chlorine and water in the liquid phase and in an acidic medium.

2. A process according to claim 1, in which the reaction is carried out in the presence of sulphuric acid, nitric acid, hydrochloric acid, phosphoric acid, methanesulphonic acid, acetic acid and/or organic or inorganic acids containing fluorine and/or chlorine.

3. A process according to claim 1, in which at least 3.5 moles of water are employed per mole of bis-(trifluoromethyl-)disulphane.

4. A process according to claim 1, in which at least 4 moles of chlorine are employed per mole of bis-(trifluoromethyl-)disulphane.

5. A process according to claim 1, which is carried out at temperatures in the range from $-18°$ to $+120°$ C.

6. A process according to claim 1, which is carried out in the presence of fluorinated sulphonamides as catalyst.

7. A process according to claim 1, which is carried out at a pressure of 1 to 100 bar.

8. A process according to claim 1, in which the reaction mixture is worked up by phase separation and/or distillation.

9. A process according to claim 1, wherein 0.1 to 20 parts by weight of acid, calculated as 100% strength acid, are employed per part by weight of the disulphane.

10. A process according to claim 2, wherein the sulphuric acid is aqueous sulphoric acid with a concentration of 5 to 70% by weight, wherein the nitric acid is aqueous nitric acid with a concentration of 5 to 90% by weight, wherein the hydrochloric acid is aqueous hydrochloric acid with a concentration of 5 to 39% by weight, wherein the phosphoric acid is aqueous phosphoric acid with a concentration of 30 to 85% by weight, and wherein the acetic acid is aqueous acetic acid with a concentration of 30 to 95% by weight.

11. A process according to claim 1, wherein the acid is fluoroacetic acid is selected from the group consisting of difluoroacetic acid, and trifluoroacetic acid.

12. A process according to claim 11, wherein the fluoroacetic acid is aqueous fluoroacetic acid with a concentration of 5 to 100% by weight.

13. A process according to claim 1, wherein the acid is a chloroacetic acid selected from the group consisting of monochloroacetic acid, dichloroacetic acid and trichloroacetic acid.

14. A process according to claim 1, wherein the chloroacetic acid is aqueous chloroacetic acid with a concentration of 5 to 95% by weight.

15. A process according to claim 1, which further consists essentially of conducting the reacting in the presence of a solvent.

* * * * *